United States Patent
Weiβ et al.

(10) Patent No.: US 7,820,845 B2
(45) Date of Patent: Oct. 26, 2010

(54) PREPARATION OF PHOSPHORUS-CONTAINING PROPOXYLATION PRODUCTS BY USING ALUMINIUM TRICHLORIDE

(75) Inventors: Thomas Weiβ, Ilvesheim (DE); Rainer Elbert, Gladbach (DE)

(73) Assignee: LANXESS Deutschland GmbH, Leverkusen (DE)

( * ) Notice: Subject to any disclaimer, the term of this patent is extended or adjusted under 35 U.S.C. 154(b) by 166 days.

(21) Appl. No.: 12/011,551

(22) Filed: Jan. 28, 2008

(65) Prior Publication Data

US 2008/0227997 A1 Sep. 18, 2008

(30) Foreign Application Priority Data

Feb. 2, 2007 (DE) .................. 10 2007 005 273
Feb. 9, 2007 (DE) .................. 10 2007 006 494

(51) Int. Cl.
  *C07F 9/06* (2006.01)
(52) U.S. Cl. ..................................... 558/203
(58) Field of Classification Search .................. 558/203
  See application file for complete search history.

(56) References Cited

U.S. PATENT DOCUMENTS

| | | | |
|---|---|---|---|
| 2,610,978 A | 9/1962 | Lanham | 260/461 |
| 3,100,220 A | 8/1963 | Smith | 260/461 |
| 5,627,299 A * | 5/1997 | Tokuyasu et al. | 558/91 |
| 2006/0211877 A1 | 9/2006 | Weiss et al. | 558/106 |

FOREIGN PATENT DOCUMENTS

| | | |
|---|---|---|
| DE | 1 921 504 | 11/1972 |
| DE | 1 25 035 | 3/1977 |
| EP | 0 398 095 | 5/1990 |
| EP | 1702923 A2 | 9/2006 |

OTHER PUBLICATIONS

Tokuyasu et al., 1996, CAS: 125:301239.*
Boghosian, S. et al: "Characterization of 1-5, 8, 9 vapor complexes over molten phosphoryl Chloride-aluminum or gallium chloride mixtures: Raman spectra and thermodynamics" Polyhedron, 12(7) pp. 771-782, (1993) XP-002507679.
Gutmann V.; "Verbindungen des Phosphoroxychlorids und das Verhalten ihrer Lösungen" Z. Anorg. Allg. Chem. Nr. 269, (1952) pp. 279-291 XP-002507678.
Methoden der Organischen Chemie, Houbel-Weyl; Muller E.; vol. 12/2, pp. 336-339 (1964).
European Search Report from corresponding EP application No. 09176233.6, dated Mar. 9, 2010, consisting of 4 pages.
Gutmann, V., "Verbindungen des Phosphoroxychlorids und das Verhalten ihrer Losungen", Z. Anorg. Alleg. Chem, Nr. 269, 1952, 279-291.
Boghosian, S., et al., "Characheristization of vapor complexes over molten phosphoryl chloride-aluminum or gallium chloride mixtures: Raman spectra and thermodynamics", Polyhedron, 12(7), 771-82, 1993.

* cited by examiner

*Primary Examiner*—Rei-tsang Shiao
(74) *Attorney, Agent, or Firm*—Michael A. Miller

(57) ABSTRACT

The invention describes a process for preparing propoxylated, phosphorus-containing compounds using aluminium chloride catalyst.

5 Claims, 3 Drawing Sheets

PREPARATION OF PHOSPHORUS-CONTAINING PROPOXYLATION PRODUCTS BY USING ALUMINIUM TRICHLORIDE

The invention relates to a process for preparing phosphorus-containing propoxylation products having an advantageous isomer ratio by means of aluminium chloride as catalyst, and also to the use thereof as polymer additives, for example as flame retardants, in polyurethanes.

BACKGROUND OF THE INVENTION

The preparation of phosphorus-containing alkoxylation products, more particularly of organic phosphonates and halogen-substituted alkyl phosphates, is know to the skilled worker. Primarily phosphoric acid, phosphorous acid or phosphorus trihalide, preferably phosphorus trichloride, or phosphorus oxyhalide, more particularly phosphorus oxychloride, are used and are reacted with epoxides such as ethylene oxide, propylene oxide and/or epichlorohydrin. To increase the reaction rate it is common to use catalysts. For catalysts which operate homogeneously there are numerous versions known to the skilled worker.

Generally speaking, the alkoxylated products obtained have to be purified over a number of stages at different pH levels. The aftertreatment is usually accomplished by an aqueous workup of the crude reaction products, in the course of which the catalyst is destroyed irreversibly and is separated off. Aftertreatments of this kind for destroying or deactivating the catalyst, however, have drawbacks. They additionally necessitate reactors. There is a deterioration in the space/time yield, and losses of product occur. The washing water which is obtained must be disposed of, which is costly and inconvenient.

This is described, for example, in DD 125 035, where deactivation and/or destruction of the titanium halide catalyst employed therein is achieved by adding a stoichiometric amount of water or by scrubbing the phosphorus-containing alkoxylation products with water or alkalis.

The use of different catalysts in the reaction of phosphorus oxychloride with higher alkylene oxides such as propylene oxide generally results in a diastereomer mixture of the tris (chloropropyl) phosphates [referred to hereinbelow as TCPP]. In the course of this reaction the oxirane ring in propylene oxide is opened, with formation of TCPP. The choice of catalyst here has a critical influence on the ratio of the TCPP isomers (I) to (IV) to one another (see below). Furthermore, the choice of catalyst may also have a beneficial effect on the spectrum of by-products of the reaction, such as, for example chloropropanols, TCPP ethers (TCPP ethers=phosphates of I-IV with chlorinated polyether functions instead of chloropropyl), 2-methylpentenal, etc.

U.S. Pat. No. 3,100,220 discloses the use of titanium tetrachloride for preparing TCPP. This gives a TCPP having a specific density of 1.294. No composition of the isomers is disclosed.

DE-A 1 921 504 discloses a process for preparing chloroalkyl ester compounds with pentavalent phosphorus. A process is claimed for preparing chloroalkyl ester compounds with pentavalent phosphorus using aqueous titanium trichloride solutions in the form of a 0.001% by weight aqueous solution of $TiCl_3$ that contains hydrochloric acid. No isomer composition of the TCPP is disclosed.

U.S. Pat. No. 2,610,978 describes the unadvantageous use of aluminium trichloride. It mentions the risk of an uncontrollable reaction between ethylene oxide and phosphorus oxychloride as a result of precipitating catalyst. The catalyst concentration has been disclosed at between 0.3% and 1% relative to the reaction product. A TCPP obtained from $TiCl_4$ catalysis was described with a refractive index of $n_D^{30}$: 1.4608. No isomer distribution of the TCPP was specified.

EP 0 398 095 A2 discloses a process for preparing TCPP using titanium tetrachloride. The process is claimed for a phosphorus oxychloride/propylene oxide ratio of 1:3.09 to 1:3.50 mol/mol at 80-95° C. and a catalyst concentration of 1.7 to $2.8 \cdot 10^{-3}$ mol/mol $POCl_3$. The workup concerns a three-stage water scrub consisting of acid, neutral and alkali scrub with subsequent drying of the product. No precise product analysis of the TCPP is disclosed.

It was an object of the present invention, then, to develop a process for preparing phosphorus-containing alkoxylation products using a catalyst which ideally yields an optimized isomer ratio with as few secondary components as possible and hence with better yields. A low spectrum of secondary components, such as the TCPP ether content, for example, is critically important in respect of an advantageous toxicological evaluation. Furthermore, the process ought to operate with a minimum of scrubbing steps needed, and hence ought to be sparing in its use of resources.

SUMMARY OF THE INVENTION

Figure 1:
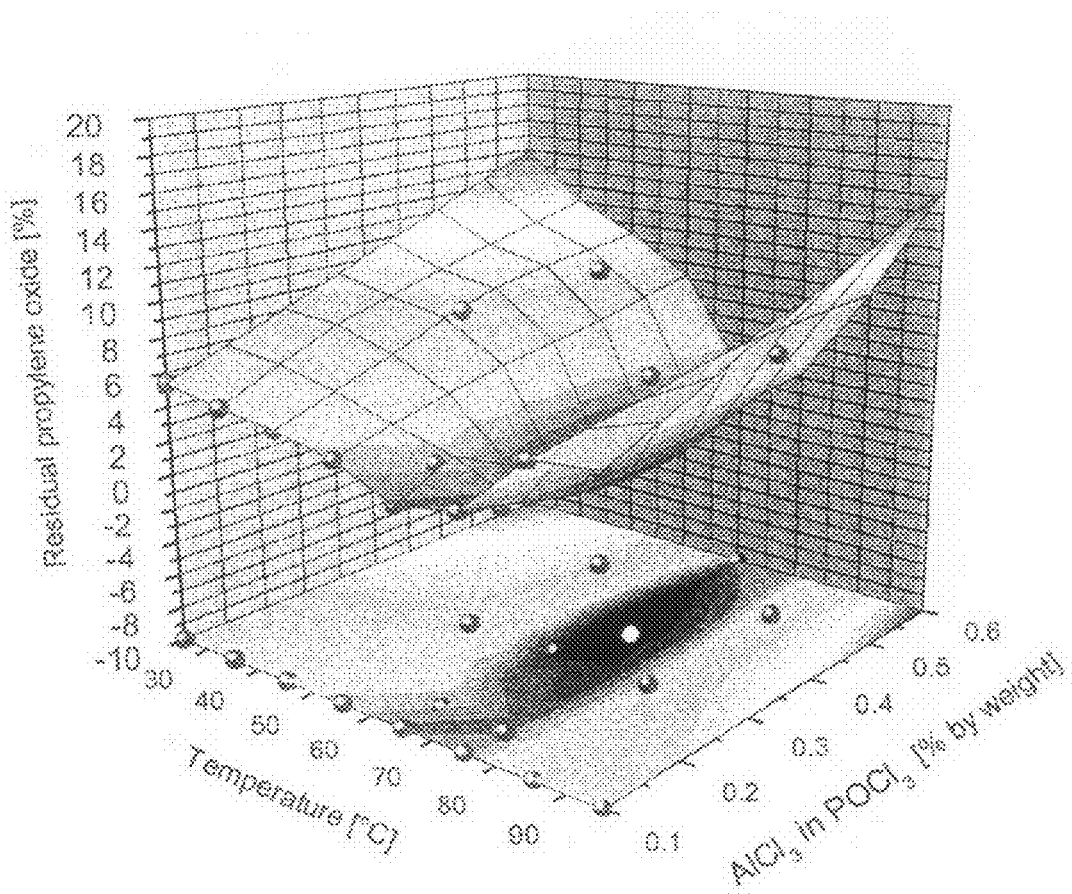
FIG. 1 illustrates propylene conversion in synthesis according to the present invention.

The achievement of the object and hence the subject of the present invention is a process for preparing phosphorus-containing propoxylation products of low acid content and having a defined isomer ratio by reacting phosphorus trihalides and/or phosphorus-oxyhalides with alkylene oxides, characterized in that a) first of all the phosphorus trihalides and/or oxyhalides are reacted continuously with aluminium trichloride, b) the reaction product from a) is transferred batchwise or continuously to a reactor, where it is reacted with alkylene oxides, and finally c) the crude product, following removal of excess alkylene oxide, is supplied to a single alkali metal hydroxide scrub.

Surprisingly the phosphorus-containing propoxylation products prepared by means of aluminium chloride catalyst exhibit an isomer ratio which is advantageous in comparison to the prior art while at the same time very largely avoiding the formation of by-products. The avoidance of secondary reactions, such as the formation of TCPP ether, for example, is of particular advantage in respect of the reaction yield when aluminium trichloride is employed.

It is surprising that, in the case of the inventive synthesis of TCPP, an isomer mixture of the compounds (I) to (IV) is obtained

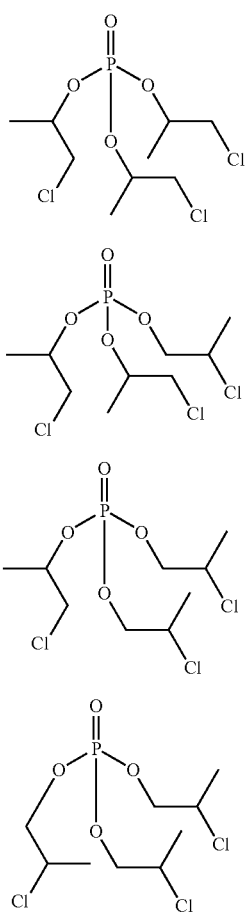

in which the ratio of the isomers (I)/(II) in the mixture is >4, preferably 4 to 6. When aluminium chloride is used the ratio is >4, preferably 4 to 6, and the TCPP ether content is 0.01 to 0.99%. The isomer ratio can be influenced in this reaction by temperature and catalyst content. In comparison, the ratio of the isomers (I)/(II) where titanium tetrachloride is used is <4 and the TCPP ether content is 1.5% to 2.9%.

In one preferred embodiment the process of the invention relates to the synthesis of tri(chloropropyl) phosphate (TCPP) and/or of the mixture of its configurational isomers, namely $(MeCHClCH_2O)_3PO$ (I), $(ClCH_2CH_2CH_2O)(MeCHClCH_2O)_2PO$ (II), $(ClCH_2CH_2CH_2O)_2(MeCHClCH_2O)PO$ (III), $(ClCH_2CH_2CH_2O)_3PO$ (IV).

Preferably the ratio of the isomers (I)/(II) in the TCPP isomer mixture is 4 to 6 and the fraction of isomer (I) is 70% to 90%. With particular preference this ratio is achieved through the employment of aluminium trichloride. All % figures in the present specification denote % by weight.

Phosphorus-containing reactants used in the process of the invention are preferably phosphorus trihalides and/or oxyhalides, more particularly phosphorus trichloride and/or phosphorus oxychloride, and they are reacted individually or in a mixture with one another with the alkylene oxides in the presence of aluminium trichloride. Examples of alkylene oxides are ethylene oxide, propylene oxide, styrene oxide, cyclohexene oxide, cyclopentene oxide, glycidyl ether, epichlorohydrin, epoxidized polybutadiene, and epoxidized unsaturated oils. The alkylene oxides here may also be used in a mixture with one another with the phosphorus trihalides and/or oxyhalides. In this way it is possible to obtain phosphorus-containing alkoxylation products such as tri(chloropropyl) phosphate (TCPP), tri(chloroethyl) phosphate (TCEP), tri(chloropropyl) phosphite or tri(chloroethyl) phosphite, for example.

In one preferred embodiment step b) uses propylene oxide and/or ethylene oxide as the alkylene oxide.

The implementation of step b) and of step c), where the latter step is carried out, is known to the skilled worker from, for example, *Methoden der Organischen Chemie, Houben-Weyl*, Vol. 12/2 pp. 336-339.

The process of the invention for preparing phosphorus-containing alkoxylation products by means of aluminium chloride catalyst can be carried out both continuously and batchwise. In view of step a) the process is preferably carried out continuously. Prior to the reaction of phosphorus trihalide and/or oxyhalide with alkylene oxides, the aluminium trichloride is preferably contacted with the phosphorus trihalides and/or oxyhalides in a dissolution vessel, and the attendant reaction product $POCl_3.AlCl_3$ (*Z. Anorg. Allg. Chem.* 1952, 269, 279) is supplied together with excess phosphorus trihalide and/or zeilxyhalide to the reactor for the reaction with an alkylene oxide.

The temperature during the dissolving operation on the aluminium trichloride in step a) ought to be situated in the range from 0 to 200° C., preferably 10 to 150° C., with particular preference 15 to 100° C.

The flow rate of phosphorus trihalide and/or oxyhalide over the aluminium catalyst depends on the implementation of stage b), but in order to ensure a continuous regime ought to be 100 l/h to 1000 l/h, more particularly 200 l/h to 500 l/h. After the conclusion of stage a) the aluminium trichloride content of the reaction solution is in the range from 10 to 10 000 ppm, preferably in the range from 1000 to 3000 ppm.

As already described above, the implementation of stage b) is known to the skilled worker. It is carried out at temperatures of 0 to 100° C. Preferably the reaction temperatures lie between 50 to 80° C. The reaction takes place under atmospheric pressure or under a slight overpressure of up to 1 MPa. The reaction mixture from stage a) is charged to the reaction vessel and the alkylene oxide is metered in continuously. The reaction medium can be diluted by adding phosphorus-containing alkoxylation products with one of the coreactants or separately. After the end of alkylene oxide metering an after-reaction phase is added at temperatures of 60 to 130° C., and, to conclude, volatile impurities are removed by vacuum distillation and/or nitrogen stripping at temperatures of 90 to 150° C. and pressures of up to <0.05 MPa. Preferably removal of volatile constituents takes place at about 130° C. and about 40 mbar.

Further advantages of the process of the invention based on aluminium chloride catalyst lie in the ease with which the catalyst can be separated from the reaction products. This is done by utilizing the property whereby aluminium ions ($Al^{3+}$) are soluble in alkali scrubs in the form of soluble aluminium complexes, e.g. $[Al(OH)_4]^-$. In the case of other catalysts, in contrast, generally non-amphoteric metal salts, such as those of titanium (III) or titanium (IV), it is necessary first of all to perform acidic scrubs in order to convert the non-amphoteric metal ions into a water-solid form. Subsequently, in a neutral scrub and an alkali scrub, acidic constituents, such as residual acid, more particularly bis(chloropropyl) phosphoric acid, are neutralized again, so as to give an acid-free end product. In contrast to this, it is possible through the use of aluminium trichloride to implement the metal salt and the neutralization in one step. Hence it is possible, in a way which is sparing with resources, to forgo a costly and inconvenient multistage scrub. At the same time, purer products and less polluted wastewaters are obtained.

The present invention also relates, however, to phosphorus-containing propoxylation products of low acid content and having a defined isomer ratio, obtainable by reacting phosphorus trihalides and/or oxyhalides with alkylene oxides, characterized in that
a) first of all the phosphorus trihalides and/or oxyhalides are reacted continuously with aluminium trichloride,
b) the reaction product from a) is transferred batchwise or continuously to a reactor, where it is reacted with alkylene oxides, and finally
c) the crude product, following removal of excess alkylene oxide, is supplied to a single alkali metal hydroxide scrub.

Finally the present invention relates to the use of aluminium chloride for preparing phosphorus-containing propoxylation products of low acid content and having a defined isomer ratio, characterized in that
a) first of all the phosphorus trihalides and/or oxyhalides are reacted continuously with aluminium trichloride,
b) the reaction product from a) is transferred batchwise or continuously to a reactor, where it is reacted with alkylene oxides, and finally
c) the crude product, following removal of excess alkylene oxide, is supplied to a single alkali metal hydroxide scrub.

EXAMPLES

Example 1

Synthesis of tris(chloropropyl)phosphate (TCPP)

Figure 2:
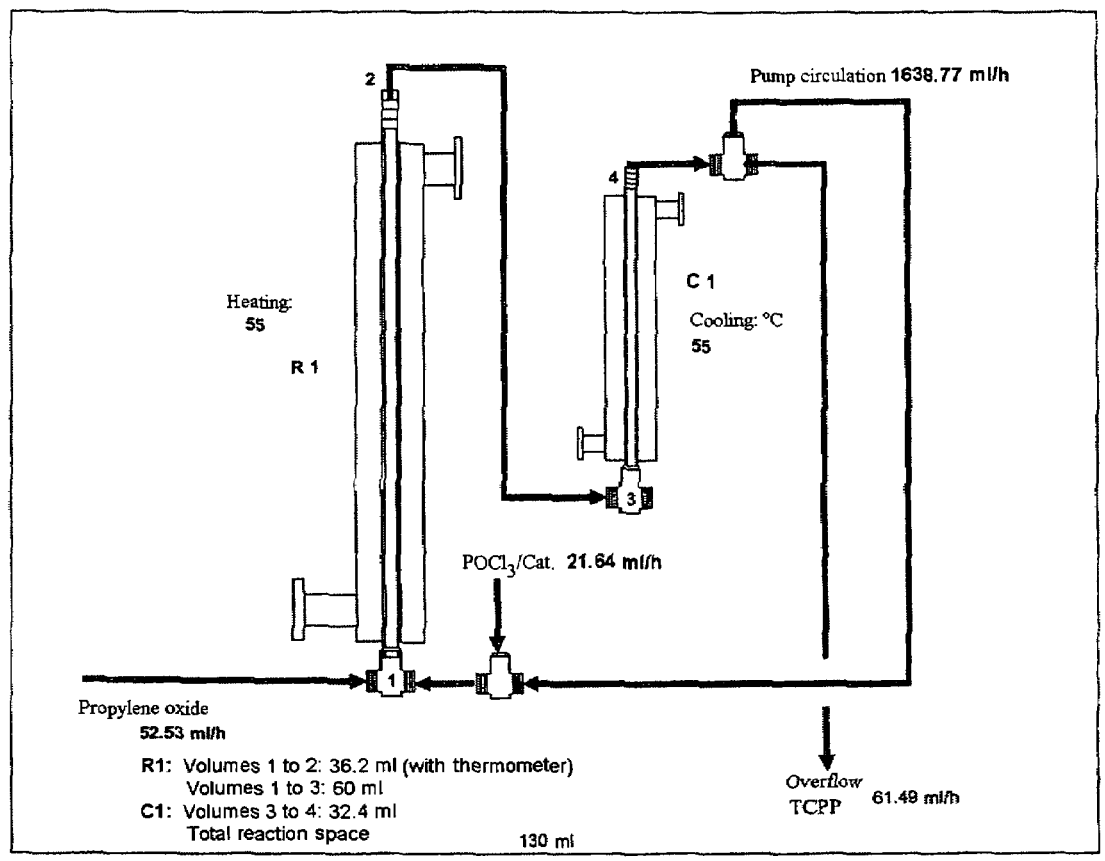
FIG. 2 illustrates a reactor for synthesis of compounds according to the present invention.

The reactor (FIG. 2) charged with tris(chloropropyl) phosphate was fed continuously with propylene oxide (52.5 ml/h) and aluminium trichloride in solution in phosphorus oxychloride (21.6 ml/h). The reaction was carried out with a pump circulation rate of 1638 ml/h. The catalyst concentration was varied, as was the reaction temperature. After a run time of 6 h, samples of the tris(chloropropyl) phosphate discharged were taken, and the product composition was analysed by gas chromatography. Table 1 shows the conversion of the reaction, measured as residual propylene oxide (GC%), and the isomer composition, both as a function of the catalyst concentration and the reaction temperature. A depiction of the propylene conversion from Table 1 in graph form can be seen in FIG. 1.

TABLE 1

| Temperature [° C.] | % by weight $AlCl_3$ in $POCl_3$ | GC % residual propylene oxide | (I)* | (II)* | Ratio (I)/(II) | (III)* | (IV)* | TCPP ether* |
|---|---|---|---|---|---|---|---|---|
| 55 | 0.15 | 13.1 | 81.0 | 17.6 | 4.58 | 1.2 | 0.02 | 0.18 |
| 65 | 0.15 | 3.6 | 82.0 | 16.6 | 4.95 | 1.2 | 0.03 | 0.16 |
| 75 | 0.15 | 2.3 | 80.5 | 17.9 | 4.50 | 1.4 | 0.03 | 0.16 |
| 65 | 0.30 | 0.1 | 81.8 | 16.8 | 4.85 | 1.3 | 0.03 | 0.09 |
| 65 | 0.60 | 2.4 | 80.6 | 17.6 | 4.57 | 1.4 | 0.04 | 0.36 |
| 25 | 0.10 | 5.4 | 83.2 | 15.7 | 5.30 | 1.0 | 0.00 | 0.12 |
| 35 | 0.10 | 4.8 | 84.2 | 14.9 | 5.66 | 0.9 | 0.00 | 0.00 |
| 45 | 0.10 | 4.4 | 83.2 | 15.8 | 5.27 | 0.9 | 0.00 | 0.12 |
| 55 | 0.10 | 3.7 | 82.0 | 16.7 | 4.92 | 1.2 | 0.00 | 0.12 |
| 65 | 0.10 | 2.2 | 80.9 | 17.7 | 4.56 | 1.3 | 0.00 | 0.11 |
| 75 | 0.10 | 2.9 | 79.5 | 18.9 | 4.21 | 1.5 | 0.00 | 0.11 |
| 85 | 0.10 | 6.4 | 76.1 | 21.5 | 3.54 | 2.0 | 0.12 | 0.24 |
| 95 | 0.10 | 6.8 | 71.2 | 24.9 | 2.86 | 2.9 | 0.15 | 0.74 |
| 50 | 0.30 | 9.0 | 81.8 | 16.5 | 4.94 | 1.2 | 0.03 | 0.44 |
| 50 | 0.50 | 9.3 | 80.7 | 17.3 | 4.65 | 1.4 | 0.04 | 0.59 |
| 80 | 0.30 | 7.4 | 79.4 | 18.4 | 4.32 | 1.6 | 0.04 | 0.61 |
| 80 | 0.50 | 6.1 | 78.2 | 19.0 | 4.08 | 1.7 | 0.05 | 0.99 |

*Relative fractions, standardized without propylene oxide.

Example 2

Synthesis of tris(chloropropyl) phosphate (TCPP)

The reactor (FIG. 2) charged with tris(chloropropyl) phosphate was fed continuously with propylene oxide (52.5 ml/h) and the catalyst titanium tetrachloride or aluminium chloride, in solution in phosphorus oxychloride (21.6 ml/h). The reaction was carried out with a pump circulation rate of 1638 ml/h in reactor 1. The catalyst concentration was varied, as was the reaction temperature. After 6 h in each case a sample of 250 ml of tris(chloropropyl) phosphate was taken. Following removal of volatile constituents under reduced pressure on a rotary evaporator (80° C., 15 mbar, 0.5 h), the product composition was analysed by gas chromatography (GC) (Table 2).

Subsequently the products were purified in a three-stage water scrub. This was done by combining the sample of 250 ml of 5-molar HCl in a vol/vol ratio of 1:1 at 90° C. Following phase separation, the organic phase was washed with water, 0.2 m aqueous sodium hydroxide solution, and again with water, in each case in a vol/vol ratio of 1:1 at 90° C. After phase separation, the products were dried on a rotary evaporator for 2 h at 80° C. and 15 mbar and were analysed by gas chromatography, and their physical parameters were ascertained as well (Table 3).

TABLE 2

| Temp. [° C.] | AlCl$_3$ [mol %] in POCl$_3$ | TiCl$_4$ [mol %] in POCl$_3$ | Propylene oxide | (I) | (II) | (III) | (IV) | Ratio (I)/(II) | TCPP ether | 2-Methyl-pentenal |
|---|---|---|---|---|---|---|---|---|---|---|
| 55 | 0.52 | — | 0.1 | 81.0 | 16.7 | 1.3 | 0.04 | 4.9 | 0.3 | 0.07 |
| 50 | 0.52 | — | 0.0 | 81.5 | 16.4 | 1.2 | 0.03 | 5.0 | 0.2 | 0.05 |
| 40 | 0.52 | — | 0.1 | 82.1 | 15.7 | 1.1 | 0.03 | 5.2 | 0.2 | 0.06 |
| 55 | 0.34 | — | 0.1 | 81.5 | 16.2 | 1.2 | 0.03 | 5.0 | 0.1 | 0.06 |
| 55 | 0.11 | — | 0.1 | 82.5 | 15.9 | 1.1 | 0.02 | 5.2 | 0.1 | 0.02 |
| 65 | 0.11 | — | 0.0 | 78.0 | 18.3 | 1.6 | 0.05 | 4.3 | 0.4 | 0.04 |
| 65 | — | 0.52 | 0.1 | 69.7 | 23.0 | 2.8 | 0.13 | 3.0 | 2.3 | 0.15 |
| 50 | — | 0.52 | 0.1 | 73.0 | 21.3 | 2.3 | 0.09 | 3.4 | 1.9 | 0.07 |
| 40 | — | 0.52 | 0.1 | 73.7 | 20.3 | 2.0 | 0.06 | 3.6 | 1.5 | 0.07 |
| 65 | — | 0.34 | 0.1 | 68.0 | 22.6 | 2.9 | 0.13 | 3.0 | 2.6 | 0.17 |
| 65 | — | 0.11 | 0.1 | 57.0 | 21.6 | 2.8 | 0.15 | 2.6 | 2.9 | 0.05 |

TABLE 3

Reaction conditions at 65° C., 0.34 mol % catalyst in POCl$_3$.

| | | Before scrub | | After scrub | |
|---|---|---|---|---|---|
| Product spectrum GC [%] | | Comparative Example: TiCl$_4$ | AlCl$_3$ | Comparative Example: TiCl$_4$ | AlCl$_3$ |
| Propylene oxide | | 0.1 | 0.09 | <0.01 | 0 |
| 2-Chloropropanol | | 0.6 | 0.26 | <0.01 | 0 |
| 1,2-Dichloropropane | | 0.1 | 0.02 | | 0 |
| 2-Methyl-2-pentenal | | 0.2 | 0.08 | 0.1 | 0.04 |
| OP(OIso)$_3$ (I) | | 65.3 | 78.82 | 66.5 | 79.15 |
| OP(OIso)$_2$(ON) (II) | | 26.3 | 18.52 | 26.1 | 18.68 |
| OP(OIso)(ON)$_2$ (III) | | 4.0 | 1.57 | 3.9 | 1.59 |
| OP(ON)$_3$ (IV) | | 0.2 | 0.05 | 0.3 | 0.05 |
| TCPP ether | | 2.4 | 0.29 | 2.9 | 0.31 |
| Residue | | 0.9 | 0.4 | | |
| Acid number | mg KOH/g | | | 0.01 | 0.005 |
| Hazen colour number | | | | 20 | 15 |
| Water | % | | | 0.05 | 0.04 |
| Density 20° C. | g/cm$^3$ | | | 1.288 | 1.2914 |
| Refractive index | | | | 1.464 | 1.4647 |
| Viscosity | mPas | | | ~90 | 91 |
| Conductivity | μS | | | 1 | 0.6 |

Example 3

Scrubbing of TCPP

Example 2 (reaction conditions at 65° C., 0.34 mol % catalyst in POCl$_3$) was repeated and the crude TCPP from the aluminium trichloride or titanium tetrachloride catalysis was subjected, in contrast to Example 2, to a single-stage scrub with 0.2 N NaOH at 90° C. This was done by admixture of 250 ml of crude TCPP with the same volume of 0.2 N NaOH. After phase separation, the organic phases were dried on a rotary evaporator for 2 h at 80° C. and 15 mbar and analysed by gas chromatography (Table 4).

Figure 3:
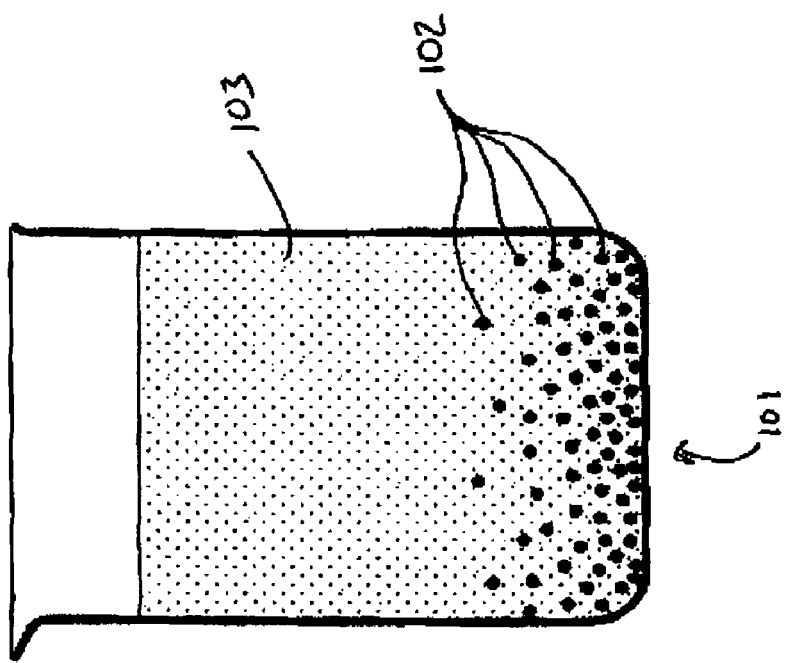
FIG. 3 illustrates a comparison using catalysts according to the prior art and those according to the present invention.
Figure 3:
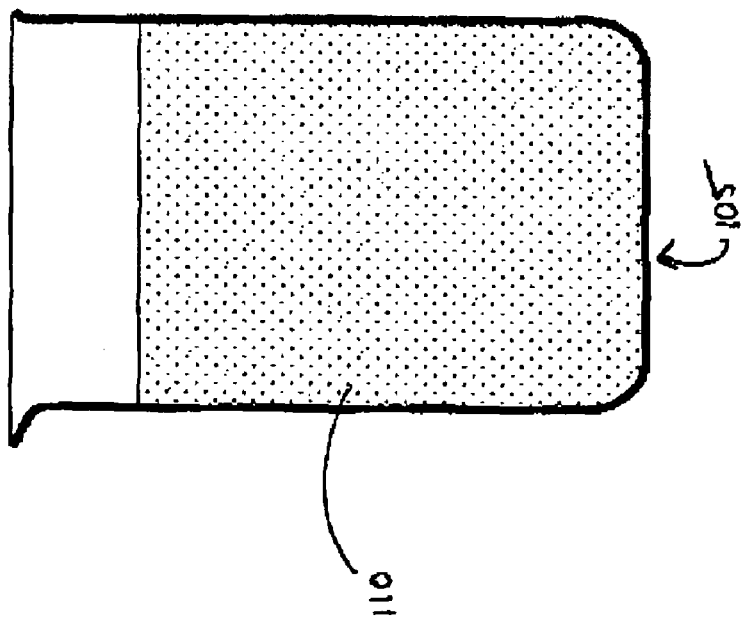

The workup of TCPP from the titanium catalysis led to formation of insoluble constituents 102 in the aqueous phase 103, as illustrated in the right beaker 101. In contrast, for the aluminium trichloride-catalysed TCPP a transparent aqueous phase 110 was obtained which was easy to separate off, as illustrated in the left beaker 105 (FIG. 3, left). The characterization of the aqueous phase is given in Table 5.

TABLE 4

| | After scrub | |
|---|---|---|
| Product spectrum GC [%] | Comparative Example: TiCl$_4$-TCPP* | AlCl$_3$-TCPP* |
| Propylene oxide | 0.00 | 0.00 |
| 2-Chloropropanol | 0.01 | 0.00 |
| 1,2-Dichloropropane | 0.00 | 0.00 |
| 2-Methyl-2-pentenal | 0.03 | 0.00 |
| OP(OIso)$_3$ (I) | 67.31 | 79.10 |
| OP(OIso)$_2$(ON) (II) | 26.09 | 18.66 |
| OP(OIso)(ON)$_2$ (III) | 3.75 | 1.59 |
| OP(ON)$_3$ (IV) | 0.19 | 0.05 |
| TCPP ether | 2.50 | 0.31 |
| Residue | 0.11 | 0.30 |
| Metal content [ppm]** | <1 | 2 |

*Average values from two experiments in each case;
**Detection limit: 1 ppm

TABLE 5

| | After scrub | |
|---|---|---|
| Analytical data for the aqueous phase [ppm] | Comparative Example: TiCl$_4$-TCPP* | AlCl$_3$-TCPP* |
| Chloride (Cl$^-$) | 3860 | 1335 |
| Organic carbon (homogenized)** | 3910 | 2170 |
| AOX (adsorbable organic halogens)** | 1650 | 1400 |

*Average values from two experiments in each case;
**Detection limit: 10 ppm

What is claimed is:

1. A process for preparing phosphorus-containing propoxylation products of low acid content and having a defined isomer ratio by reacting phosphorus trihalides and/or phosphorus oxyhalides with alkylene oxides, comprising:
   a) reacting all the phosphorus trihalides and/or oxyhalides continuously with aluminium trichloride,
   b) transferring the reaction product from a) batchwise or continuously to a reactor, where it is reacted with alkylene oxides forming a crude product, and
   c) supplying the crude product, following removal of excess alkylene oxide, to a single alkali metal hydroxide scrub.

2. A process according to claim 1, wherein a product mixture with the isomers (I) to (IV) is obtained from the reaction of phosphorus oxychloride with propylene oxide,

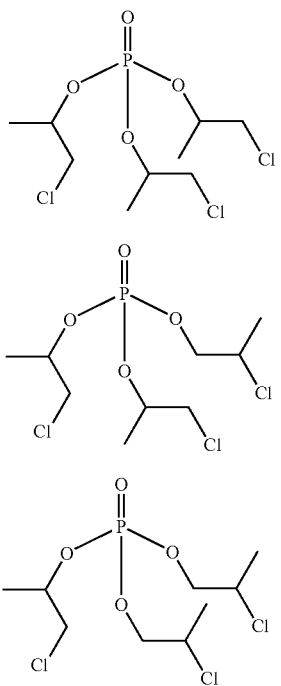

(I)

(II)

(III)

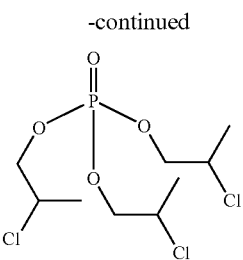

(IV)

in which the ratio of the isomers (I)/(II) in the mixture is >4 and the fraction of isomer (I) in the TCPP isomer mixture is at least 70%.

3. A process according to claim 1, wherein in step a) the phosphorus trihalides and/or oxyhalides are reacted continuously with aluminium trichloride at temperatures of 25 to 80° C., using 0.05 to 5 mol % of aluminium trichloride relative to phosphorus trihalides and/or oxyhalides, and in step b) the reaction product from a) is transferred batchwise or continuously to a reactor, where it is reacted with propylene oxide.

4. A process according to claim 3, wherein step b) is followed by a single alkali scrub c).

5. A process according to claim 3, wherein propylene oxide and other alkylene oxides are used in a mixture.

* * * * *